United States Patent [19]

Leuchs et al.

[11] Patent Number: 4,952,730
[45] Date of Patent: Aug. 28, 1990

[54] PROCESS FOR INVERTING THE CONFIGURATION OF OPTICALLY ACTIVE COMPOUNDS, AND OPTICALLY ACTIVE INTERMEDIATES PRODUCED IN THIS PROCESS

[75] Inventors: Hans-Jürgen Leuchs, Bad Soden am Taunus; Werner Mohler, Hofheim am Taunus; Hanns-Eberhard Erle, Frankfurt am Main, all of Fed. Rep. of Germany

[73] Assignee: Hoechst Aktiengesellschaft, Frankfurt am Main, Fed. Rep. of Germany

[21] Appl. No.: 868,889

[22] Filed: May 27, 1986

Related U.S. Application Data

[63] Continuation of Ser. No. 519,746, Aug. 2, 1983, abandoned.

[30] Foreign Application Priority Data

Aug. 4, 1982 [DE] Fed. Rep. of Germany ....... 3229046

[51] Int. Cl.$^5$ .................... C07C 82/00; C07D 263/12
[52] U.S. Cl. .................................. 564/302; 548/239; 564/304; 564/349
[58] Field of Search ...................... 564/302, 304, 345; 548/239

[56] References Cited

U.S. PATENT DOCUMENTS

| | | | |
|---|---|---|---|
| 2,446,192 | 8/1948 | Pfister et al. | 548/239 X |
| 2,513,346 | 7/1950 | Moersch et al. | 548/239 X |
| 2,530,627 | 11/1950 | Pfister et al. | 548/239 X |
| 4,237,304 | 12/1980 | Dowd et al. | 548/239 |
| 4,391,980 | 7/1983 | Zergenyi | 548/239 |

FOREIGN PATENT DOCUMENTS

7605A1 3/1981 European Pat. Off. .

OTHER PUBLICATIONS

Chem. Abs. 84 (7): 43593 x (1976)–Abstract of Japanese Patent 74 75,545 to Muro et al., for Inverting Steric Configurations of Aminoalcohols.

*Primary Examiner*—Robert V. Hines
*Attorney, Agent, or Firm*—Finnegan, Henderson, Farabow, Garrett, and Dunner

[57] ABSTRACT

The invention relates to a process for inverting the configuration at the optically active carbon atom (*) in compounds of the formula I

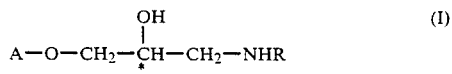

in which A denotes a carbocyclic or heterocyclic aromatic radical and R denotes an aliphatic, cycloaliphatic or araliphatic hydrocarbon radical, by formylation, treating the resulting compounds with a strong acid or an acid halide and cleaving the oxazolinium derivatives thus obtained, by acid or alkaline hydrolysis, if appropriate via the stage of the N-formyl compound, and to oxazolinium derivatives of the formula III defined herein and formed as intermediate products.

4 Claims, No Drawings

PROCESS FOR INVERTING THE CONFIGURATION OF OPTICALLY ACTIVE COMPOUNDS, AND OPTICALLY ACTIVE INTERMEDIATES PRODUCED IN THIS PROCESS

This is a continuation of Ser. No. 519,746, filed Aug. 2, 1983, and now abandoned.

The invention relates to a process for inverting the configuration at the optically active carbon (*) in compounds of the formula I

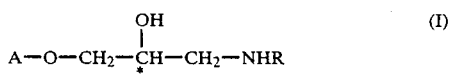

in which A represents an optionally substituted carbocyclic or heterocyclic aromatic radical and R represents hydrogen or an optionally substituted aliphatic, cycloaliphatic or araliphatic hydrocarbon radical, which comprises converting compounds of the formula I by formylation into optically active compounds of the formula II

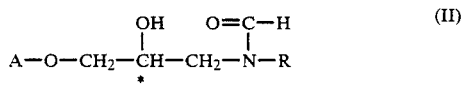

in which A and R have the meanings defined above, while maintaining the configuration at the carbon atom (*), converting these compounds, by treatment with a strong acid or an acid halide, into optically active cyclic compounds of the formula III

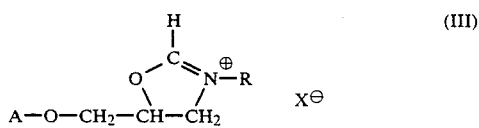

in which A and R have the meanings defined above and in which $X^\ominus$ represents the anion of a strong acid or of a halogen atom, and converting these oxazolinium derivatives (III), by acid or alkaline hydrolysis, if appropriate via the stage of the N-formyl compound, into optically active compounds of the formula IV

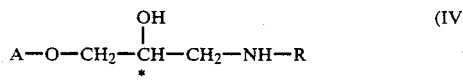

in which A and R have the meanings defined above, possessing the same structure as the starting material I, but having an opposite configuration at the carbon atom (*), and, if desired, converting a free compound of the formula I into a salt or converting a resulting salt into the free compound.

The inversion of configuration according to the invention relates to the secondary alcohol group which is present in the group

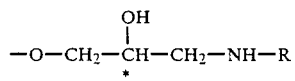

and which contains a chirality center and can therefore exist either in the S-configuration or in the R-configuration.

Accordingly, a (2S)-3-amino-2-propanol of the formula I is converted by the process according to the invention into the corresponding (2R)-3-amino-2-propanol, or a (2R)-3-amino-2-propanol of the formula I is converted into the corresponding (2S)-3-amino-2-propanol. If no further chirality center is present in a compound of the formula I, this inversion of configuration effects an inversion in the direction of optical rotation.

Carbocyclic aromatic radicals A are, in particular, phenyl and also, if appropriate, partially saturated, bicyclic aromatic hydrocarbon radicals, such as, for example, naphthyl, 1,2,3,4-tetrahydro-5-naphthyl, 1,2,3,4-tetrahydro-6-naphthyl, 4-indenyl, 5-indenyl, 4-indanyl or 5-indanyl, and also, if appropriate, partially saturated polycyclic aromatic hydrocarbon radicals, such as, for example, 4-fluorenyl or 9,10-ethano-9,10-dihydro-1-anthryl, partially saturated radicals of the above type being attached to the oxygen atom via a ring carbon atom in the aromatic part.

Heterocyclic radicals A of aromatic character contain, as ring hetero-atoms, primarily one or more ring nitrogen atoms, ring sulfur atoms or ring oxygen atoms and also, preferably in addition to a ring nitrogen atom, a ring oxygen or ring sulfur atom. Radicals of this type are, in particular, five-membered or six-membered monocyclic structures containing 1,2 or 3 ring hetero-atoms. Radicals which are particularly preferred are six-membered monocyclic structures containing 1 ring nitrogen atom, such as, for example, 2-, 3- or 4-pyridyl, six-membered monocyclic structures containing 2 ring nitrogen atoms, such as, for example, 3-pyridazinyl, 2-pyrimidinyl, 4-pyrimidinyl or 2-pyrazinyl, five-membered monocyclic structures containing one ring sulfur atom, such as, for example, 2-thienyl or 3-thienyl, five-membered monocyclic structures containing one sulfur atom and 2 nitrogen atoms in the ring, such as, for example, 1,2-thiadiazol-3-yl, if appropriate, partially saturated bicyclic structures containing 1 ring nitrogen atom and containing a five-membered or six-membered heterocyclic ring, such as, for example, 4-indolyl or 1,2,3,4-tetrahydro-5-quinolinyl, or bicyclic structures of a partially aromatic character containing 1 ring sulfur atom, such as, for example, 2H-8-thiochromenyl.

The above radicals A can be unsubstituted or substituted, and A can preferably contain one substituent, but can also contain several, in particular two, substituents. Preferred substituents are optionally substituted aliphatic or cycloaliphatic hydrocarbon radicals, optionally etherified or esterified hydroxyl or mercapto groups, acyl radicals, optionally functionally modified carboxyl groups, such as, for example, carboxamido, nitrile or ester groups, nitro groups or optionally substituted amino groups. In addition to the substituents indicated above, saturated parts of the group A can also contain substituents attached by a double bond, in particular oxo.

As substituents of the radical A, aliphatic hydrocarbon radicals are, in particular, $(C_1-C_7)$-alkyl or $(C_2-C_7)$-alkenyl and also $(C_2-C_7)$-alkynyl. Substituents of these radicals are optionally etherified or esterified hydroxyl or mercapto, for example $(C_1-C_7)$-alkoxy, $(C_1-C_7)$-alkylthio or halogen, optionally functionally modified carboxyl, in particular optionally N-substituted carbamoyl such as N-$(C_1-C_7)$-alkylated carbamoyl, optionally N-substituted carboxamido or optionally substituted amino, in particular acylamino in which acyl represents the radical of an organic carboxylic acid or of a carbonic acid half-derivative, and of an organic sulfonic acid, or optionally N-substituted or N'-lower-alkylated ureido, and also ($C_1$–$C_7$)-alkylsulfonylamino. Substituted ($C_1$–$C_7$)-alkyl radicals are primarily hydroxy-($C_1$–$C_6$)-alkyl, ($C_1$–$C_7$)-alkoxy-($C_1$–$C_6$)-alkyl, ($C_1$–$C_7$)-alkylthio-($C_1$–$C_6$)-alkyl, halogeno-($C_1$–$C_6$)-alkyl, optionally N-($C_1$–$C_7$)-alkylated carbamoyl-($C_1$–$C_6$)-alkyl, ($C_1$–$C_7$)-alkanoylamino-($C_1$–$C_6$)-alkyl or ($C_1$–$C_7$)-alkoxycarbonylamino-($C_1$–$C_6$)-alkyl, and also cyano-($C_2$–$C_6$)-alkenyl and also ($C_1$–$C_7$)-alkanoylamino-($C_2$–$C_7$)-alkenyl or ($C_1$–$C_7$)-alkoxycarbonylamino-($C_2$–$C_7$)-alkenyl.

As substituents on the radical A, cycloaliphatic hydrocarbon radicals are to be understood as meaning, in particular, monocyclic cycloalkyl and also polycyclic cycloalkyl. Cycloalkyl having 4–7 C atoms, in particular cyclopentyl, is preferred.

As substituents of a radical A, etherified hydroxyl or mercapto groups are above all hydroxyl or mercapto etherified by the aliphatic or cycloaliphatic, optionally substituted, hydrocarbon radicals defined above, such as, for example, ($C_1$–$C_7$)-alkoxy, ($C_4$–$C_7$)-cycloalkoxy or phenyl-($C_2$–$C_6$)-alkoxy, ($C_2$–$C_7$)-alkenyloxy or ($C_2$–$C_7$)-alkynyloxy, and also tetrahydrofurfuryloxy, ($C_1$–$C_7$)-alkylthio or ($C_2$–$C_6$)-alkenylthio.

As substituents of groups A, examples of esterified hydroxyl or mercapto groups are ($C_1$–$C_7$)-alkanoyloxy. Acyl groups as defined above are, inter alia, ($C_1$–$C_7$)-alkanoyl. Optionally functionally modified carboxyl groups as defined above are, in particular, carboxamido, alkoxycarbonyl, carbamoyl or cyano. Esterified carboxyl is preferably ($C_1$–$C_7$)-alkoxycarbonyl Amidated carboxyl is optionally substituted carbamoyl.

Optionally substituted amino groups as defined above are, in particular, acylamino in which acyl represents primarily the corresponding radical of an organic ($C_1$–$C_7$)-carboxylic acid or of a half-derivative of carbonic acid and also of an organic ($C_1$–$C_7$)-sulfonic acid. As radical A there is preferred in particular the phenyl groups substituted with a ($C_4$–$C_7$)-cycloalkyl group or a cyano-($C_2$–$C_4$)-alkenyl group.

Aliphatic hydrocarbon radicals R are primarily ($C_1$–$C_7$)-alkyl radicals which, in particular, are branched at the linking carbon, such as, for example, tert.-butyl, and also ($C_2$–$C_7$)-alkenyl or ($C_2$–$C_7$)-alkynyl radicals. Cycloaliphatic hydrocarbon radicals R are, in particular, cycloalkyl, including polycyclic cycloalkyl, and araliphatic hydrocarbon radicals R are primarily phenyl-($C_2$–$C_7$)-alkyl or heterocyclo-($C_2$–$C_7$)-alkyl, such as, for example, 2-indolyl-($C_2$–$C_7$)-alkyl or 3-indolyl-($C_2$–$C_7$)-alkyl. Examples of substituents of such hydrocarbon radicals are, for ($C_1$–$C_7$)-alkyl, etherified hydroxyl, in particular phenoxy or pyridyloxy which is optionally substituted, for example by functionally modified carboxyl, such as optionally N-($C_1$–$C_7$)-alkylated carbamoyl, for example carbamoyl, N-($C_1$–$C_7$)-alkylcarbamoyl or N,N-di-($C_1$–$C_7$)-alkylcarbamoyl, or optionally functionally modified carboxyl, such as carboxyl, esterified carboxyl, for example ($C_1$–$C_7$)-alkoxycarbonyl, amidated carboxyl, such as optionally N-lower-alkylated carbamoyl for example carbamoyl, N-($C_1$–$C_7$)-alkylcarbamoyl or N,N-di-($C_1$–$C_7$)-alkylcarbamoyl, or cyano, while examples for the aromatic part of phenyl- ($C_2$–$C_7$)-alkyl are ($C_1$–$C_7$)-alkoxy, ($C_1$–$C_7$)-alkylamino or optionally functionally modified carboxyl, primarily amidated carboxyl, such as carbamoyl which is optionally substituted by ($C_1$–$C_7$)-alkyl, such as N-($C_1$–$C_7$)-alkylcarbamoyl or N,N-di-($C_1$–$C_7$)-alkylcarbamoyl, and/or hydroxyl. ($C_1$–$C_6$)-Alkyl radicals which are substituted in this manner are phenoxy-($C_1$–$C_6$)-alkyl or, preferably, optionally N-alkylated carbamoylphenoxy-($C_1$–$C_6$)-alkyl, and also pyridyloxy-($C_1$–$C_6$)-alkyl or, preferably, optionally N-($C_1$–$C_7$)-alkylated carbamoyl-pyridyloxy-($C_1$–$C_6$)-alkyl, and also ($C_1$–$C_7$)-alkoxycarbonyl-($C_1$–$C_6$)-alkyl, optionally N-($C_1$–$C_7$)-alkylated carbamoyl-($C_1$–$C_6$)-alkyl or cyano-($C_1$–$C_6$)-alkyl.

As radicals R there are in particular preferred ($C_3$–$C_4$)-alkyl radicals which are branched at the linking carbon atom, especially the tert.-butyl radical and the phenylethyl groups substituted with one or preferably two ($C_1$–$C_2$)-alkoxy groups.

A process for inverting the configuration of optically active compounds is known from European Patent No. A1 0,007,605. In this process an optically active compound is converted into the corresponding N-acyl derivative of the formula V.

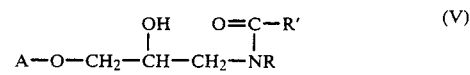

In this process R' is a monocyclic or polycyclic, carbocyclic or heterocyclic radical or an optically substituted aliphatic, cycloaliphatic or araliphatic hydrocarbon radical.

The N-acyl derivative (V) is cyclized to give the corresponding oxazolinium salt of the formula VI

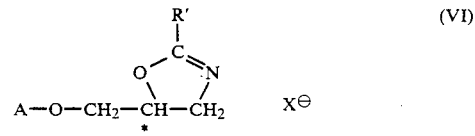

which is then hydrolyzed to give an optically active compound having the same structure, but the opposite configuration to that of the starting material.

In attempts to apply this process to the conversion of 1-aryloxy-3-tert.-butylamino-2-propanols, it has now been found that, using known acylating agents, such as, for example, acetic acid, acetic anhydride, ethyl acetate or acetyl chloride, 1-aryloxy-3-tert.-butylamino-2-propanols of this type (R=tert.-butyl) can only be converted into compounds of the formula (V) (R'=CH$_3$) in yields of less than 5%, even if reacted for several days. Hence it was no longer possible either to prepare the cyclic intermediate products (VI) (R'=CH$_3$) which are required for inverting the configuration, in satisfactory yields; a useful inversion o configuration could not be achieved in this way.

It has now been found, surprisingly, that 1-aryloxy-3-tert.-butylamino-2-propanols of this type, of the formula I, can be converted in good yields in accordance with methods which are in themselves known by means of formylating agents into the corresponding N-formyl compounds of the formula II, which can then be cyclized to give the corresponding oxazolinium salts of the formula III, either in the melt or in a suitable solvent, by means of a strong acid or by means of an acid halide, at temperatures from −20° C. to +150° C., preferably at 0° to 50° C.

These salts are hydrolyzed in an acid or basic medium, if appropriate via the stage of the inverted N-formyl compound, to give an optically active 1-aryloxy-3-tert.-butylamino-2-propanol of the formula (IV) having the same structure but the opposite configuration to that of the starting material of the formula I.

It has also been found that this process for inverting the configuration of optically active compounds by formylation, cyclization and hydrolysis is not limited to 1-aryloxy-3-tert.-butylamino-2-propanols, but is applicable very generally to optically active compounds of the formula (I)

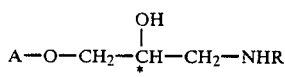

in which A and R have the meaning defined initially.

A further advantage of the new process is the use of formic acid or derivatives thereof as the reagent for the preparation of the intermediate products, since formic acid and its derivatives are readily available and (on a quantity basis) are generally cheaper than the homologous carboxylic acids and corresponding derivatives thereof.

Examples of suitable formylating agents are formic acid or derivatives thereof (for example the mixed anhydride formed from formic acid and acetic anhydride, phenyl formate, methyl formate, ethyl formate and butyl formate). Instead of the pure formic acid esters, it is also possible to prepare the latter in situ by azeotropic esterification and to employ them without further purification for formylating the amino-2-propanols of the formula I.

Suitable cyclizing reagents are strong, oxygen containing inorganic or organic acids, such as, for example, concentrated sulfuric acid or phosphoric acid or a strong organic sulfonic acid, for instance an aliphatic sulfonic acid, for example methanesulfonic acid, or an aromatic sulfonic acid, such as an optionally substituted phenylsulfonic acid or halides thereof, primarily the chlorides or bromides, such as thionyl chloride, thionyl bromide, sulfuryl chloride, chlorosulfonic acid, phosphorus trichloride, phosphorus pentachloride, phosphorus oxychloride or methanesulfonyl chloride. Furthermore, it is also possible to use mixed esters corresponding to the said halides, such as, for instance, a lower alkoxysulfonyl halide or phosphorus acid lower alkyl ester-halides. The cyclization is carried out either in the melt or in a suitable inert solvent (for example methylene chloride or toluene).

If acids are used, a temperature range from 50° to 150° C. is preferred, while if an acid chloride is used it is preferable to carry out the reaction at −20° to 80° C.

The hydrolysis is carried out in an acid or basic medium. Acid agents suitable for the hydrolysis are aqueous acids, for instance aqueous mineral acids, for example aqueous hydrochloric acid, sulfuric acid or phosphoric acid. The acid hydrolysis is carried out within a temperature range from 0° to +120° C., advantageously at 10° to +50° C. Examples of suitable basic media are aqueous alkaline solutions, for instance those of the alkali or alkaline earth metals, such as sodium hydroxide or potassium hydroxide or the hydroxides of calcium or magnesium, and it is advantageous to employ the said reagents at an elevated temperature, for instance within a range from 50° to 150° C. The hydrolysis can be carried out in a homogeneous phase as well as in a multiphase system.

The process according to the invention can also be carried out without isolating the intermediate product of the formula II, which is then processed further in the same reaction mixture to give the compound of the formula III, and the resulting compound of the formula III is subjected to hydrolysis without further purification.

The invention also relates to optically active compounds of the formula III in which A, R and $X^{\ominus}$ have the above meanings or to such compounds in the form of free bases.

Preferred compounds of the formula III are those in which A represents optionally substituted phenyl, as defined above, R represents alkyl, preferably branched at the point of attachment, and $X^{\ominus}$ represents an anion of sulfuric acid, phosphoric acid or a strong organic sulfonic acid, such as p-toluenesulfonic acid or benzenesulfonic acid, or a chloride or bromide.

Owing to their pharmacological properties the compounds of formula IV can be used as medicaments.

The examples which follow serve to illustrate the invention without limiting it to the compounds mentioned as representatives:

EXAMPLE 1

The inversion of (+)-1-(2-cyclopentylphenoxy)-3-tert.-butylamino-2-propanol (a)

(+)-1-(2-Cyclopentylphenoxy)-3-N-tert.-butyl-N-formyl-amino-2-propanol

A solution in 60 g of methyl formate of 29.1 g of 1-(2-cyclopentylphenoxy)-3-tert.-butylamino-2-propanol (81% (+)-configuration and 19% (−)-configuration, $[\alpha]_D^{20}$ +100° Uo-(5% strength in isopropanol)) is heated under reflux for 48 hours. The crude (+)-1-(2-cyclopentylphenoxy)-3-N-tert.-butyl-N-formylamino-2-propanol is obtained after evaporating the solution in vacuo. This compound can be recrystallized from n-hexane ($[\alpha]_D^{20}$+11.0°).

(b)

1-tert.-Butyl-4-(2-cyclopentylphenoxymethyl)-oxazolinium chloride.

The crude (+)-1-(2-cyclopentylphenoxy)-3-N-tert.-butyl-N-formylamino-2-propanol is dissolved in 50 ml of toluene. 7.5 ml of thionyl chloride are added dropwise to this solution, while cooling with ice, at such a rate that the temperature does not exceed 20° C. Stirring is continued for 15 minutes, and the crude 1-tert.-butyl-3-(2-cyclopentylphenoxymethyl)-oxazolinium chloride is obtained after evaporating the solution in vacuo.

The crude oxazolinium salt can be recrystallized from toluene ($[\alpha]_D^{20}$+8.2°).

(c)

(−)-1-(2-Cyclopentylphenoxy)-3-tert.-butylamino-2-propanol

The crude 1-tert.-butyl-4-(2-cyclopentylphenoxymethyl)-oxazolinium chloride is dissolved in 60 ml of isopropanol, 400 ml of 4N sodium hydroxide solution are added and the mixture is boiled under reflux for 3 hrs. while stirring vigorously. After cooling to room temperature, the organic phase is separated off.

It contains 27.0 g of 1-(2-cyclopentylphenoxy)-3-tert.-butylamino-2-propanol (67% (−)-configuration and 33% (+)-configuration, $[\alpha]_D^{20} = -5.5°$ (measured in a 5% strength solution of isopropanol; content of base determined titrimetrically using hydrochloric acid)). This corresponds to an optical yield of 55%. The isopropanol solution is filtered and 12.2 g of D-(−)-mandelic acid are added to the filtrate, whereupon (−)-1-(2-cyclopentylphenoxy)-3-tert.-butylamino-2-propanol D-(−)-mandelate is precipitated, which is purified by recrystallization from 50 ml of isopropanol.

Yield: 22.0 g ($[\alpha]_D^{20} = -52.4°$ (1% strength solution in isopropanol)), $\simeq 61.3\%$ of the (+)-base present in the starting material and $\simeq 74.1\%$ of the (−)-base present in the saponification solution.

EXAMPLE 2

The inversion of (+)-1-(2-cyclopentylphenoxy)-3-tert.-butylamino-2-propanol

(a)

(+)-1-(2-Cyclopentylphenoxy)-3-N-tert.-butyl-N-formylamino-2-propanol 291.0 g of 1-(2-cyclopentylphenoxy)-3-tert.-butylamino-2-propanol (81% (+)-configuration and 19% (−)-configuration, $[\alpha]_D^{20} = +10.0°$ (5% strength in isopropanol)) and 306 g of butyl formate are heated at reflux temperature for 6 hours. The crude (+)-1-(2-cyclopentylphenoxy)- 3-N-tert.-butylamino-N-formylamino-2-propanol is obtained after evaporating the reaction mixture in vacuo.

(b)

1-tert.-Butyl-4-(2-cyclopentylphenoxymethyl)-oxazolinium chloride

The crude (+)-1-(2-cyclopentylphenoxy)-3-N-tert.-butyl-N-formylamino-2-propanol is dissolved in 240 ml of toluene. 95 ml of thionyl chloride are added, while cooling, to this solution at such a rate that the temperature does not exceed 40° C. Stirring is continued for 2 hours at this temperature.

(c)

(−)-1-(2-Cyclopentylphenoxy)-3-tert.-butylamino-2-propanol

The solution in toluene of the crude 1-tert.-butyl-4-(2-cyclopentylphenoxymethyl)-oxazolinium chloride is subjected to acid hydrolysis by adding this solution dropwise to 100 ml of water at such a rate that the temperature does not exceed 60° C. Stirring is continued for 2 hours at 60° C. and 800 ml of 18% strength sodium hydroxide solution are then added. The toluene phase is separated off, washed with 100 ml of water and filtered; it contains 280.2 g of (−)-1-(2-cyclopentyl-phenoxy)-3-tert.-butyl-amino-2-propanol (titrated with hydrochloric acid). $[\alpha]_D^{20}: -8.2°$ (5% strength in isopropanol; 76% (−)-configuration and 24% (+)-configuration) Optical yield: 82%.

Further purification is effected via the diastereomeric salt with D-(−)-mandelic acid, as described in Example 1 (c).

EXAMPLE 3

The inversion of (+)-1-(2-cyclopentylphenoxy)-3-tert.-butylamino-2-propanol

(a)

(+)-1-(2-Cyclopentylphenoxy)-3-N-tert.-butyl-N-formylamino-2-propanol

A mixture of 110 g of 85% strength formic acid, 148 g of n-butanol and 35 g of toluene is heated under a water separator. After 2 hrs. 50 ml of water (containing 11% of formic acid) have been separated off and a clear distillate runs off. 291 g of 1-(2-cyclopentylphenoxy)-3-tert.-butylamino-2-propanol (81% (+)-configuration and 19% (−)-configuration, $[\alpha]_D^{20} + 10.0°$ (5% strength in isopropanol)) are added to the solution, and the mixture is heated under reflux for 16 hours. The solvents (butyl. formate, butanol and toluene) are removed, first under normal pressure and then in vacuo; crude (+)-1-(2-cyclopentylphenoxy)-3-N-tert.-butyl-N-formylamino-2-propanol is obtained.

The mixture of solvents which has been removed can be re-used for further similar reactions after replenishing the formic acid.

Further working up is carried out as described in Example 2 (b) and 2 (c). The toluene solution contains 271.2 g of (−)-1-(2-cyclopentylphenoxy)-3-tert.-butylamino-2-propanol (titrated with hydrochloric acid).

$[\alpha]_D^{20}: -7.2°$ (5% strength in isopropanol; 73% (−)-configuration and 27% (+)-configuration).

Optical yield: 72%.

EXAMPLE 4

The inversion of (+)-1-(2-cyclopentylphenoxy)-3-tert.-butylamino-2-propanol

(a)

(+)-1-(2-Cyclopentylphenoxy)-3-N-tert.-butyl-N-formylamino-2-propanol 145.5 g or 1(2-cyclopenxylphenoxy)-3-tert.-butylamino-2-propanol (81% (+)-configuration and 19% (−)-configuration, $[\alpha]_D^{20} = 10.0°$ (5% strength in isopropanol)) are dissolved in 172 ml of toluene, and 54.1 g of 85% strength formic acid are added dropwise at room temperature. The mixture is heated for approx. 7 hours under a water separator, in which time 31 g of water (containing approx. 60% of formic acid) are separated off. After removing the solvent and excess formic acid by vacuum distillation, the crude (+)-1-(2-cyclopentylphenoxy)-3-N-tert.-butyl-N-formylamino-2-propanol is left as the residue.

(b)

1-tert.-Butyl-4-(2-cyclopentylphenoxymethyl)-oxazolinium chloride 37.5 ml of thionyl chloride are added dropwise, while cooling to a solution of the crude (+)-1-(2-cyclopentylphenoxy)-3-N-tert.-butyl-N-formylamino-2-propanol in 150 ml of toluene at such a rate that the temperature does not exceed 40° C. Stirring is then continued for 2 hours at this temperature.

(c)
(−)-1-(2-Cyclopentylphenoxy)-3-tert.-butylamino-2-propanol

The solution in toluene of the crude 1-tert.-butyl-3-(2-cyclopentylphenoxymethyl)-oxazolinium chloride is added dropwise, while stirring, to 50 ml of water at such a rate that the temperature does not exceed 60° C. The solution is stirred for a further 2 hours at 60° C., and 375 ml of 18% strength sodium hydroxide solution are then added. The organic phase is separated off, washed with 50 ml of water and filtered; it contains 130.9 g of (−)-1-(2-cyclopentyl-phenoxy)-3-tert.-butylamino-2-propanol (titrated with hydrochloric acid). $[\alpha]_D^{20}$: −5.7° (5% strength in isopropanol; 68% (−)-configuration and 32% (+)-configuration)

Optical yield: 57%.

Further purification is effected via the diastereomeric salt with D-(−)-mandelic acid, as described in Example 1 c).

EXAMPLE 5

The inversion of (+) 3-{-4-[3-(3.4-dimethoxy-phenylethylamino)-2-hydroxy-propoxy]phenyl}(crotonic acid nitrile.

(a) (+) 3-{4-[3-(3.4-dimethoxyphenylethyl-N-formylamino)-2-hydroxy-propoxy]phenyl}acid nitrile.

300 g of (+)-{4-[3-(3.4-dimethoxyphenylethylamino)-2-hydroxypropoxy]phenyl}crotonic acid nitrile ($[\alpha]_D^{20}=+9,2°$ [5% strength in methanol], 98% (+)-configuration and 2% (−)-configuration) are dissolved in 2 l of toluene and 84.2 g of 100% strength formic acid are added dropwise at 60° C. The mixture is heated for 3 hours under a water separator in which time 40 g of water (containing about 70% of formic acid) are separated off. After removing the solvent and excess of formic acid by distillation the crude (+)3-{4-[3-(3.4-dimethoxyphenylethyl-N-formylamino)-2-hydroxy-propoxy]phenyl}crotonic acid nitrile is left as the residue.

(b) 5-[{4-(2-cyano-1-methylethylenyl)phenoxy}methyl]-3-(3.4-dimethoxyphenyl)ethyl-2-oxazolinium chloride.

The crude (+) 3-{4-[3(3.4-dimethoxyphenylethyl-N-formylamino)-2-hydroxy-propoxy]phenyl}(crotonic acid nitrile is dissolved in 700 ml of chloroform and 72.6 ml of thionylchloride are added dropwise at such a rate that the temperature does not exceed 40° C. Stirring is then continued for 2 hours at 40° C.

(c) (−)3-{4-[3-(3.4-dimethoxyphenylethylamino)-2-hydroxy-propoxy-]-phenyl}crotonic acid nitrile.

The solution of the crude 5-[{4-(2-cyano-1-methylethylenyl)phenoxy}methyl]-3-(3.4-dimethoxyphenyl)ethyl-2-oxazolinium chloride in chloroform is subjected to acid hydrolysis by adding to this solution 75 ml of water at such a rate that the temperature does not exceed 60° C. Stirring is continued for 2 hours at 60° C. and 300 ml of 5N sodium hydroxide solution are then added. The chloroform phase is separated off and washed once more with 200 ml of water, dried and the solvent is distilled off in vacuo. The residue is dissolved in 1.4 l of isopropanol by heating under reflux. Thereafter the solution is cooled to 0° C. for 6 hours. The precipitated (−)3-{4-[3-(3.4-dimethoxyphenylethylamino)-2-hydroxypropoxy]phenyl}crotonic acid nitrile is filtered off with suction and dried in vacuo. Yield: 261 g (chemical yield: 87%; $[\alpha]_D^{20}=−8,7°$ [5% strength in methanol]; 95% (−)-configuration and 5% (+)-configuration). Optical yield: 94%.

The solid substance is dissolved in 1,7 l of acetone, 260 g of (−)-dibenzoyl-tartaric acid are added and the whole is heated under reflux for 0.5 hours. After cooling for 12 hours at 0° C. 10.4 g of (+) 3-{-4-3-(3.4-dimethoxyphenylethylamino)-2-hydroxypropoxy]phenyl} crotonic acid nitrile-dibenzoyltartrate precipitates. The precipitate is filtered off. Dry HCl-gas is introduced into the acetonic solution while cooling at 0° C. until a pH-value of 1 is reached. Stirring is continued for 0.5 hours, the precipitate is filtered off with suction and washed with 300 ml of cold acetone. The precipitated (−) 3-{4-[3-(3.4-dimethoxyphenylethylamino)-2-hydroxypropoxy]phenyl}-crotonic acid nitrile-hydrochloride is purified by recrystallization from 1 l of ethanol.

Yield: 200.8 g $[\alpha]_D^{20}=−14.1°$ [5% strength in methanol] corresponding to 98% (−)-configuration and 2% (+)-configuration≈61% of the (+)-base present in the starting material and ≈70.5% of the (−)-base present in the saponification solution.

EXAMPLE 6

The inversion of (+) 3-{4-[3-(3.4-dimethoxyphenylethylamino)-2-hydroxypropoxy]phenyl}crotonic acid nitrile.

(a) (+) 3-{4-[3-(3.4-dimethoxyphenylethyl-N-formylamino)-2-hydroxypropoxy]phenyl}crotonic acid nitrile.

60.0 g of (+) 3-{4-[3-(3.4-dimethoxyphenylethylamino)-2-hydroxypropoxy]phenyl}(crotonic acid nitrile (96% (+)-configuration and 4% (−)-configuration, $[\alpha]_D^{20}=+8.8°$(5% strength in methanol)) and 110 g of butylformate are heated at reflux temperature for 1.5 hours. The crude (+) 3-{4-[3-(3.4-dimethoxypheynlethyl-N-formylamino)-2-hydroxypropoxy]phenyl}crotonic acid nitrile is obtained after evaporating the reaction mixture.

(b) 5-{4-(2-cyano-1-methylethylenyl]phenoxy}(methyl-3-(3.4-dimethoxyphenyl)ethyl-2-oxazolinium chloride.

The crude (+) 3-{4-[3-(3.4-dimethoxyphenylethyl-N-formylamino)-2-hydroxypropoxyphenyl}crotonic acid nitrile is dissolved in 120 ml of chloroform and 14.4 ml of thionyl chloride are added dropwise. Stirring is continued for 2 hours at 40° C.

(c) (−) 3-{4-[3-(3.4-dimethoxyphenylethylamino)-2-hydroxy-propoxy]phenyl}crotonic acid nitrile.

The chloroformic solution of the crude 5-{4-(2-cyano-1-methylethylenyl)phenoxy}methyl]-3-(3.4-dimethoxyphenyl)ethyl-oxazolinium chloride is subjected to acid hydrolysis by adding to this solution dropwise 15 ml of water at such a rate that the temperature does not exceed 60° C. Stirring is continued for 2 hours at 60° C. and 200 m of 2N sodium hydroxide solution are then added. The chloroform phase is separated off, washed with 100 ml of water and dried. The solvent is removed in vacuo. The crystalline residue is stirred with 200 ml of isopropanol for 2 hours at room temperature, then filtered off, washed with 50 ml of cold isopropanol and dried. Yield; 48.1 g $[\alpha]_D^{20}=−7.2°$ (5% strength in methanol)=80.2% chemical yield and 82% optical yield.

Further purification is effected via the diastereomeric salt with (−)-dibenzoyl-tartaric acid as described in Example 5 (c).

We claim:

1. A process for inverting the configuration at the optically active carbon atom (*) in a compound of the formula I

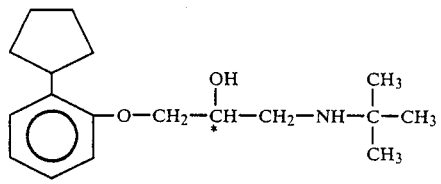
(I)

which comprises converting this compound by formylation into optically active compounds of the formula II

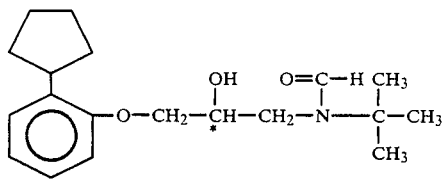
(II)

while maintaining the configuration at the carbon atom (*), converting this compound, by treatment with a strong acid or an acid halide, into optically active cyclic compounds of the formula III

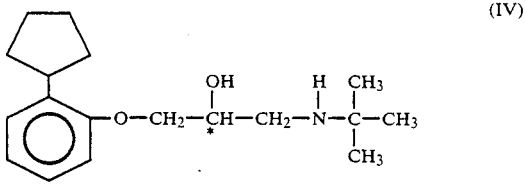
(III)

in which X⊖ represents the anion of a strong acid or a halogen atom, and converting these oxazolinium derivatives (III), by acid or alkyline hydrolysis into the optically active compound of the formula IV (IV)

possessing the same structure as the starting material I, but having an opposite configuration at the carbon atom (*).

2. The process as claimed in claim 1, wherein the acid halide used is sulfuryl chloride, thionyl bromide, thionyl chloride, phosphorus trichloride, phosphorous oxychloride, phosphorus pentachloride, toluenesulfonyl chloride or methanesulfonyl chloride.

3. The process as claimed in claim 1, wherein cyclization is carried out within the temperature range from +50° C. to 150° C. using a strong acid.

4. The process as claimed in claim 1, wherein cyclization is carried out within the temperature range from −20° to 80° C. using an acid halide.

* * * * *